US012120795B2

(12) United States Patent
Suntych

(10) Patent No.: US 12,120,795 B2
(45) Date of Patent: Oct. 15, 2024

(54) SYNCHRONIZATION OF LIGHTING NETWORKS FOR AGRICULTURE PRODUCTION

(71) Applicant: Xiant Technologies, Inc., Greeley, CO (US)

(72) Inventor: Jon Daren Suntych, Greeley, CO (US)

(73) Assignee: Xiant Technologies, Inc., Greeley, CO (US)

( * ) Notice: Subject to any disclaimer, the term of this patent is extended or adjusted under 35 U.S.C. 154(b) by 228 days.

(21) Appl. No.: 17/757,246

(22) PCT Filed: Dec. 18, 2020

(86) PCT No.: PCT/US2020/065890
§ 371 (c)(1),
(2) Date: Jun. 13, 2022

(87) PCT Pub. No.: WO2021/127358
PCT Pub. Date: Jun. 24, 2021

(65) Prior Publication Data
US 2023/0037527 A1    Feb. 9, 2023

Related U.S. Application Data

(60) Provisional application No. 62/951,241, filed on Dec. 20, 2019.

(51) Int. Cl.
*H05B 45/10*      (2020.01)
*A01G 7/04*       (2006.01)
(Continued)

(52) U.S. Cl.
CPC ........... *H05B 47/155* (2020.01); *A01G 7/045* (2013.01); *A01K 29/00* (2013.01); *A01K 29/005* (2013.01);
(Continued)

(58) Field of Classification Search
CPC .... H05B 47/10; H05B 47/105; H05B 47/155; H05B 47/16; H05B 47/19; H05B 45/00;
(Continued)

(56) References Cited

U.S. PATENT DOCUMENTS 9,526,215 B2    12/2016    Suntych
9,560,837 B1     2/2017    Suntych
(Continued)

FOREIGN PATENT DOCUMENTS

WO    2014138262 A1    9/2014
WO    2016033350 A1    3/2016
(Continued)

OTHER PUBLICATIONS

PCT/US2020/065890 Written Opinion and Search Results mailed on Apr. 28, 2021.

*Primary Examiner* — Jimmy T Vu
(74) *Attorney, Agent, or Firm* — Weatherly IP Solutions, LLC; James M. Weatherly

(57) ABSTRACT

Embodiments of the present disclosure provide systems, apparatuses and methods for synchronous communication and control of LED lights and sensors in an LED light array containing two or more LED lights. Through the use of a master clock within a gateway and/or a master controller that is in communication with LED lights in an array that is in a facility, such as in a greenhouse, hot house, poultry egg production facility, a hospital, dairy production or other lighting facilities, the gateway and/or master controller is capable of synchronizing the emission of light or photons from an LED light array by generating a master signal that contains commands and time from a master clock within the signal that is transmitted to each of the LED lights within an array.

68 Claims, 10 Drawing Sheets

(51) Int. Cl.
  *A01K 29/00* (2006.01)
  *A01K 45/00* (2006.01)
  *A61M 21/00* (2006.01)
  *A61N 5/06* (2006.01)
  *H05B 45/00* (2022.01)
  *H05B 45/14* (2020.01)
  *H05B 47/105* (2020.01)
  *H05B 47/155* (2020.01)
  *H05B 47/16* (2020.01)
  *H05B 47/19* (2020.01)

(52) U.S. Cl.
  CPC ............. *A01K 45/00* (2013.01); *A61M 21/00* (2013.01); *A61N 5/06* (2013.01); *H05B 45/00* (2020.01); *H05B 45/10* (2020.01); *H05B 45/14* (2020.01); *H05B 47/105* (2020.01); *H05B 47/16* (2020.01); *H05B 47/19* (2020.01); *A61M 2021/0044* (2013.01); *A61M 2205/3306* (2013.01); *A61M 2250/00* (2013.01); *A61N 2005/0652* (2013.01)

(58) Field of Classification Search
  CPC ........ H05B 45/14; H05B 45/10; A01G 7/045; A01K 29/00; A01K 29/005; A01K 45/00; A61M 21/00; A61M 2021/0044; A61M 2205/3305; A61N 5/06
  See application file for complete search history.

(56) References Cited

U.S. PATENT DOCUMENTS

| | | |
|---|---|---|
| 9,844,209 B1 | 12/2017 | Suntych |
| 9,907,296 B2 | 3/2018 | Suntych |
| 10,182,557 B2 | 1/2019 | Suntych |
| 10,609,909 B2 | 4/2020 | Suntych |
| 10,638,669 B2 | 5/2020 | Suntych |
| 10,709,114 B2 | 7/2020 | Suntych |
| 11,058,889 B1 | 7/2021 | Suntych |
| 11,278,009 B2 | 3/2022 | Suntych |
| 11,832,568 B2 * | 12/2023 | Suntych .................. A01G 9/20 |
| 2010/0026520 A1 | 2/2010 | Witte et al. |
| 2013/0266325 A1 | 10/2013 | Giustiniano et al. |
| 2014/0250778 A1 | 9/2014 | Suntych |
| 2017/0142940 A1 | 5/2017 | Suntych |
| 2017/0347532 A1 | 12/2017 | Suntych |
| 2019/0259108 A1 | 8/2019 | Bongartz et al. |
| 2020/0367444 A1 | 11/2020 | Suntych |
| 2023/0262865 A1 * | 8/2023 | Suntych ............... A61B 5/4306 315/312 |

FOREIGN PATENT DOCUMENTS

| | | |
|---|---|---|
| WO | 2017087077 A1 | 5/2017 |
| WO | 2018102258 A2 | 6/2018 |

* cited by examiner

SYNCHRONIZATION OF LIGHTING NETWORKS FOR AGRICULTURE PRODUCTION

CROSS REFERENCE TO RELATED APPLICATIONS

The present application claims priority to PCT application no. PCT/US20/65890, filed on Dec. 18, 2020 and U.S. Application No. 62/951,241, as filed on Dec. 20, 2019, the entire contents of both applications are incorporated herein by reference for all purposes.

BACKGROUND

The ability to synchronize the ON/OFF cycling of photon emitters has been a driving force of the lighting industry since the light bulb was first invented. Examples of synchronization include but are not limited to the ability to synchronize streetlights to correspond with day/night cycles or traffic lights to correspond with traffic patterns.

SUMMARY

The following embodiments and aspects thereof are described and illustrated in conjunction with systems, tools, and methods, which are meant to be exemplary and illustrative, not limiting in scope.

An embodiment of the present invention provides a system for synchronous control of the emission of photons from two or more LED lights, the system comprising: at least one master controller; a master clock within the at least one master controller, where the at least one master controller is capable of generating a signal transmitting the time of the master clock within the signal; two or more LED lights, where each LED light comprises: a controller; an internal clock; and at least one photon emitter, where the at least one photon emitter is capable of emission of photons; where the controller is in communication with the internal clock and the at least one photon emitter and where the time of the internal clock synchronizes the timing of the emission of photons from the at least one photon emitter; where each LED light is capable of receiving the signal from the master controller and where the controller of each LED light is capable of analyzing the time of the master clock of the signal from the master controller and comparing the time of the master clock with the time of the internal clock of the LED light.

An embodiment of the present invention provides a method of synchronizing the photon emission from two or more LED lights within an LED light array, the method comprising, providing at least one master controller, providing a master clock within the at least one master controller, where the at least one master controller is capable of generating a signal transmitting the time of the master clock within the signal, providing two or more LED lights, where each LED light comprises: a controller; an internal clock; and at least one photon emitter, where the at least one photon emitter is capable of emission of photons, where the controller is in communication with the internal clock and the at least one photon emitter and where the time of the internal clock synchronizes the timing of the emission of photons from the at least one photon emitter; generating a signal from the at least one master controller, where the signal contains the time of the master clock within the signal and the time the signal is sent: receiving the signal within each LED light; analyzing within the controller of the LED light the time of the master clock and the time the signal was sent from the master; and comparing the time of the master and the time the signal was sent from the master with the time of the internal clock of the LED light; and synchronizing the internal clock of the LED light with the master clock of the master.

An embodiment of the present invention provides a method of synchronizing the photon emission from two or more LED lights within an LED light array, the method comprising: providing at least one master controller; providing a master clock within the at least one master controller; where the at least one master controller is capable of generating a signal transmitting the time of the master clock within the signal; providing two or more LED lights, where each LED light comprises: at least one photon emitter, where the at least one photon emitter is capable of emission of photons; generating a signal from the at least one master controller, where the signal contains the time of the master clock within the signal; receiving the signal within each LED light; using said master clock to synchronize the photon emissions in each of the two or more LED lights to each other.

An embodiment of the present invention provides a method of synchronizing the photon emission from two or more LED lights within an LED light array, the method comprising: providing at least one LED light acting as a master controller; providing a master clock within the at least one master controller, where the at least one master controller is capable of generating a signal transmitting the time of the master clock within the signal; providing two or more LED lights, where each LED light comprises: at least one photon emitter, where the at least one photon emitter is capable of emission of photons; generating a signal from the at least one master controller, where the signal contains the time of the master clock within the signal; receiving the signal within each LED light; using said master clock to synchronize the photon emissions in each of the two or more LED lights to each other.

An embodiment of the present invention provides a method of synchronizing the photon emission from two or more LED lights within an LED light array within a mesh network protocol, the method comprising: providing at least one LED light acting as a master controller; providing a master clock within the at least one master controller, where the at least one master controller is capable of generating a signal transmitting the time of the master clock within the signal; providing two or more LED lights, where each LED light comprises: at least one photon emitter, where the at least one photon emitter is capable of emission of photons; generating a signal from the at least one master controller, where the signal contains the time of the master clock within the signal; receiving the signal within each LED light; using said master clock to synchronize the photon emissions in each of the two or more LED lights to each other LED light, where each other LED light in the LED light array is capable of rebroadcasting said master clock to other LED lights and adjusting its internal clock to best match said master clock and rebroadcasting it to other LED lights.

An embodiment of the present invention provides a method of synchronizing the photon emission from two or more LED lights within an LED light array within a mesh network protocol, the method comprising: providing two or more LED lights, where each LED light in the mesh network broadcasts and receives clock signals from other LED lights in the system, where each light performs a convergence algorithm to best align its internal clock to the other received clocks within the LED light array, where said LED light broadcasts its adjusted or converged clock to other LED lights within the LED light array, where over repeated cycles the clocks of all LED lights converge or align with each other, where each LED light comprises: at least one photon emitter, where the at least one photon emitter is capable of emission of photons; generating photon emissions that are synchronized to the LED light array's adjusted or converged clock.

An embodiment of the present invention provides computer readable medium comprising instructions, which when executed by one or more of the processors of a system comprising at least one master controller and two or more light emitting devices, LED, cause the system to: provide a time of a master clock within said at least one master controller; generate a signal to transmit the time of said master clock within said signal; receive the signal at the two or more LEDs, wherein each LED comprises a controller, an internal clock, and at least one photon emitter, wherein the controller of each LED is configured to synchronize a time of the internal clock of the LED with the timing of an emission of photons from said at least one photon emitter of the LED; generate a signal from said at least one master controller, wherein said signal contains the time of said master clock within said signal and a time the signal is sent: receive said signal within each LED; analyze within the controller of said LED the time of said master clock and the time the signal was sent from said master controller; and compare the time of said master clock and the time the signal was sent from said master controller with the time of the internal clock of the LED; and synchronize the internal clock of the LED with the master clock of said master controller.

Another embodiment of the present disclosure provides a method for increasing energy efficiency in a network array of photon emitters, the method comprising, providing an array photon emission housing units with a range of 20% to 80% of the units in an ON cycle and the corresponding percentage of photon emission housing units in an OFF cycle, shifting the emission housing units in an ON cycle to an OFF cycle and at the same time shifting 20% to 80% of the emission housing units in an OFF cycle to an ON cycle and repeating this cycle so that 20% to 80% of the emission housing units in an array are always in an ON cycles while a corresponding percentage are in an OFF cycle.

BRIEF DESCRIPTION OF THE FIGURES

The accompanying drawings, which are incorporated herein and form a part of the specification, illustrate some, but not the only or exclusive, example embodiments and/or features. It is intended that the embodiments and figures disclosed herein are to be considered illustrative rather than limiting.

DETAILED DESCRIPTION

Embodiments of the present disclosure provide systems, apparatuses and methods for synchronous communication and control of LED lights and sensors in an LED light array containing two or more LED lights. Through the use of a master clock within a gateway (main controller) and/or a master controller (sub-controller) that is in communication with LED lights in an array that is in a facility, such as in a greenhouse, hot house, poultry egg production facility, a hospital, dairy production or other lighting facilities, the gateway and/or master controller is capable of synchronizing the emission of light or photons from an LED light array by generating a master signal that contains commands and time from a master clock within the signal that is transmitted to each of the LED lights within an array. The signal may be transmitted by hard wire or wirelessly to the LED lights as well as sensors that support the LED light array. Each LED light and sensor receive the signal from the master or gateway and then compare the time of their internal clock with the time of the master clock signal, thus allowing the commands within the signal to be timed appropriately with the other photon emitters and sensors.

Embodiments of the present disclosure further provide systems, apparatuses, and methods for synchronization of LED light to maximize or control power efficiency. The systems, apparatuses and methods described herein reduce the power stress and heat production on a photon or light emission system, such as an array of LED light emitters in a poultry production facility, a greenhouse, a dairy barn, hog production facility, turkey production facility, cattle feed lot, cattle trailer, or a human hospital. The system and methods synchronize the emission of photons from an array of LED lights as a reduced use percentage, such as 10%, 25%, 50% or 80%, by having a corresponding percentage of LED light emitting a pulse or ON at any one time, with all LED light in an array cycling through an emission rate that is faster than the perceived optical response of an organism, reducing the power of an LED light array from 10%, 20%, 25%, 50%, 75% or 90%.

Figure 1:
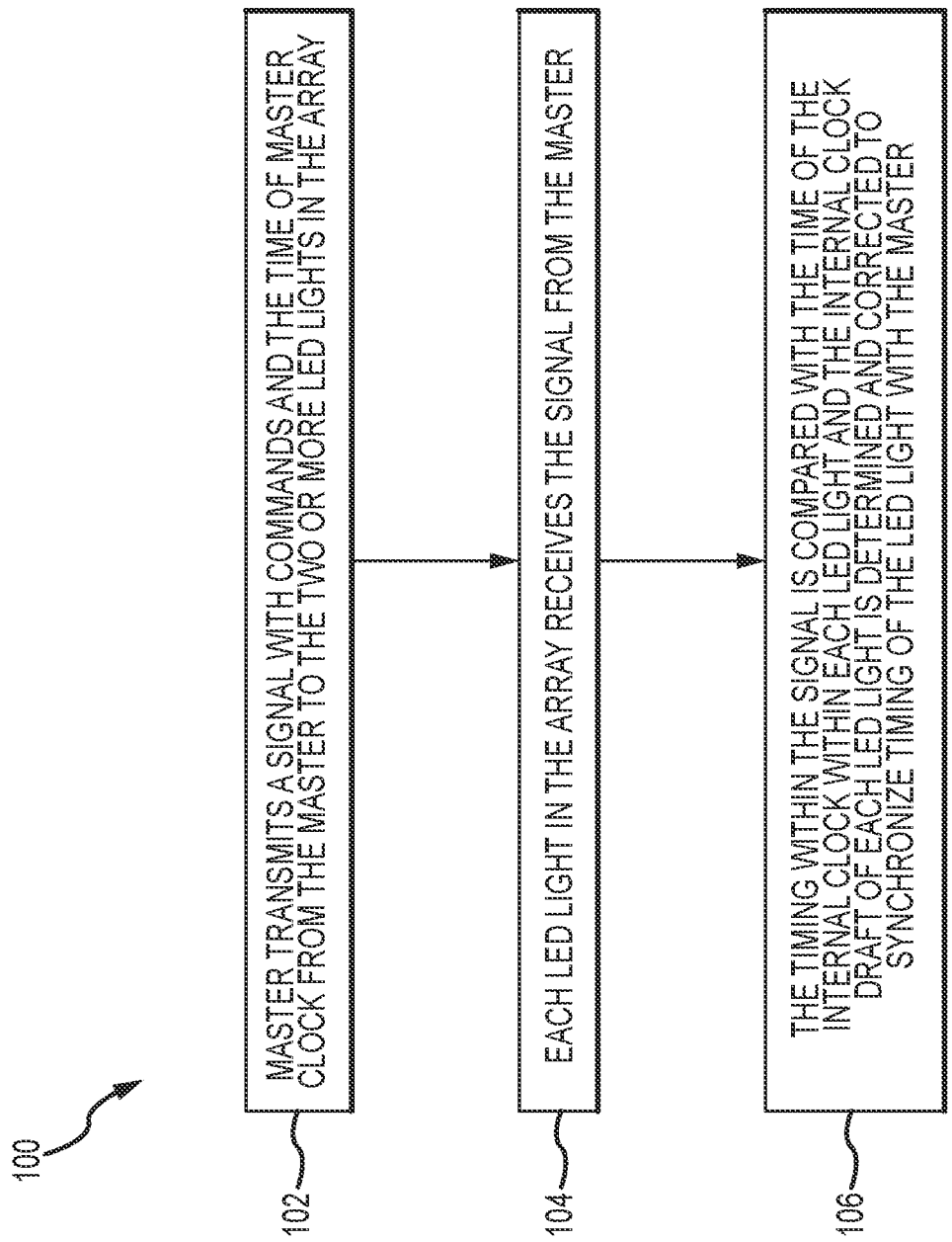
FIG. 1 is a flow diagram of a method of synchronous communication and control of photon emitters and sensor array.

FIG. 1 provides a flow chart for an example of the method of synchronous communication and control of LED light in an LED lighting array. In step 102 a master controller within a master transmits a signal with commands that include the time of a clock within the master. The signal is transmitted to the LED lights within the array by either hard wire or wireless transmission. In step 104, each LED light in the array receives the master signal which is processed within the LED light in a controller or microcontroller. In step 106, the timing from the clock within the master signal is compared with the time of the internal clock within each LED light and the internal clock drift of each internal LED light clock is determined and corrected to synchronize the LED light with the gateway and/or master controller.

Figure 2:
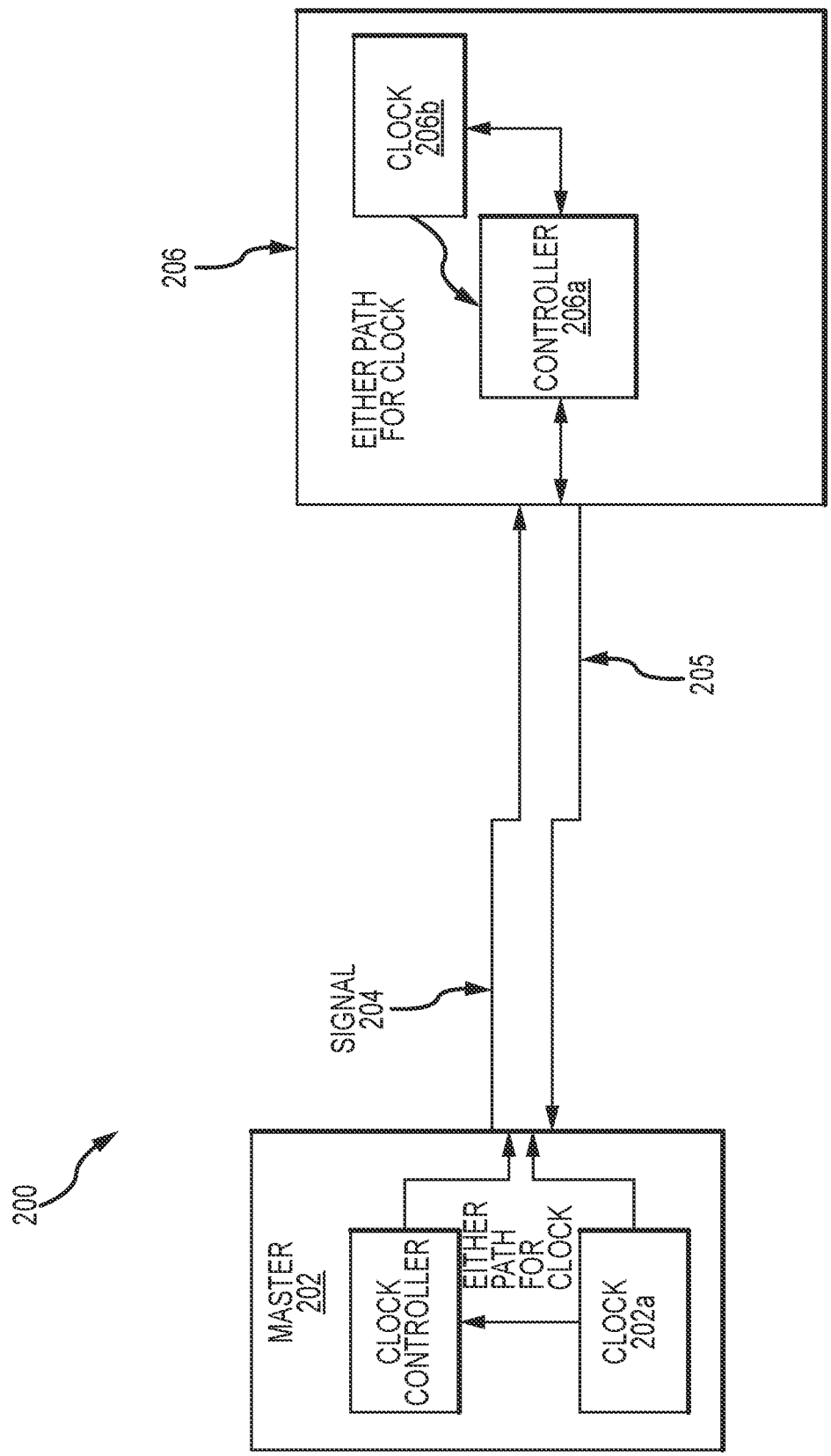
FIG. 2 is a diagram showing the communication between a master and an LED light.

FIG. 2 provides a diagram of an example of the communication between a master controller and an LED light to confirm the timing and synchronization of the LED light in relation to other LED lights that the LED light is in proximity too. As shown in FIG. 2, master 202a with a master clock 203 and an LED light 206 with an internal clock 206a are shown. A signal 204 produced is transmitted from the master 202 to the LED light 206 by the master controller. The signal 204 has a carrier frequency that is capable of containing multiple components such as commands relating to, for example: a photon emission recipe from the LED light and the time of the clock 202a within the master 202. The LED light 206 receives the signal 204 and a controller 206a within the LED light 206 compares the time of the LED light's internal clock 206b with the time of the internal clock 202a of the master 202 and the time the signal 204 was sent from the master 202. This allows the LED light to stay in synchronization with a limited clock drift up to the speed of electricity in copper. Conversely, the LED light 206 may send back to the master 202 a signal 205 with information such as a confirmation of the photon recipe, the temperature around the LED light, the time from the internal clock 206b, its offset clock adjustment of the LED light 206 and time the signal 205 is sent as well as other operating information such as noise rejection, status and health of the system or its parts and location, identification and history of itself or other LED lights and sensors in the system.

As used herein a gateway may be a networking device that provides omnidirectional control over a lighting network, a mesh network, a network of sensors, environmental controls, or a combination thereof and allows them to communicate in a synchronous manner.

As used herein, a master is a device with omnidirectional control over and communication with one or more other devices, such as a LED lights, sensor, or environmental controller.

A variety of "LED lights", light emitting device or lighting assembly having a network of lighting elements capable of a modulated emission of photons to send a repetitive pulse, waveform, or pulse train of photons, where each individual pulse comprises at least one-color spectrum, wavelength or multiple color spectrums or wavelengths and is capable varying intensities. A number of LED lights maybe used with the disclosure provided herein, as will be understood by one skilled in the art, including, but is not limited to the controlled light modulating of incandescent lights such as Tungsten-halogen and Xenon, Fluorescent (CFL's), high intensity discharge such as Metal Halide, High-Pressure Sodium, Low-Pressure Sodium, Mercury Vapor, sunlight, light emitting diodes.

The LED lights produce or emit a wavelength, wavelengths or color spectrum ranging from 0.1 to 1600 nm in width including, but not limited to, infrared, red, with near and far red (800-620 nm), orange (620-590 nm), yellow (590 to 520 nm) green, cyan (520 to 500), blue (500 to 435) violet and ultraviolet (450 to 380 nm) and white light. The LED lights produce a photon signal that may be emitted in a constant form (in conjunction with a pulsed form) or in a pulsed with "ON durations" that refer to the duration when an LED light is emitting photons or light. The ON duration for photon emission from the LED lights can be between 0.01 microseconds and 5000 milliseconds with durations of all integers in between. And the corresponding "OFF duration", which can be anywhere from 0.01 microseconds and 24 hours, with durations of all integers in between, referring to the duration where an LED light is not emitting photons or light.

A variety of signal types may be used to be broadcast from the LED lights, masters, and gateways to carry the required communication and clock time. The signal may be wired using a variety of cable, such as but not limited to, ethernet, waveguide, electrical cables for AC/DC and fiber-optic that are capable of communicating the signal or may be transmitted wirelessly, by way of example ultra-wide band, broadband, Zigbee, radio frequency (RF), passive, RFID and others that are also capable of supporting wireless communication. Additionally, the communication can be implemented on carrier frequencies across the AC or DC power lines. In this instance, the AC frequency can be utilized as the master clock frequency to the LED lights.

By way of example, a signal may be a wireless frequency in a poultry grow house in a range between 900 and 923 Mhz. Channel 0 will be 905, channel 1 will be 907 Mhz and channel 2 will be 909 Mhz. Frequency 905 Mhz is a wireless signal transmitted from the master to each LED light with a carrier frequency that can contain commands and other information relating to, for example: a photon emission recipe containing pulse duration for each component of the photon emission/signal from the LED light; OFF duration of each component; wavelength color of each component and intensity, and the time of the master clock and the time the signal was sent from the master clock. Conversely, the LED light may send back to the master controller or other LED lights a wireless signal on the same frequency 905 Mhz with the confirmation of the recipe, temperature around the LED light, the time from the internal clock, the clock adjustment of the LED light and time the signal is sent.

Figure 3:
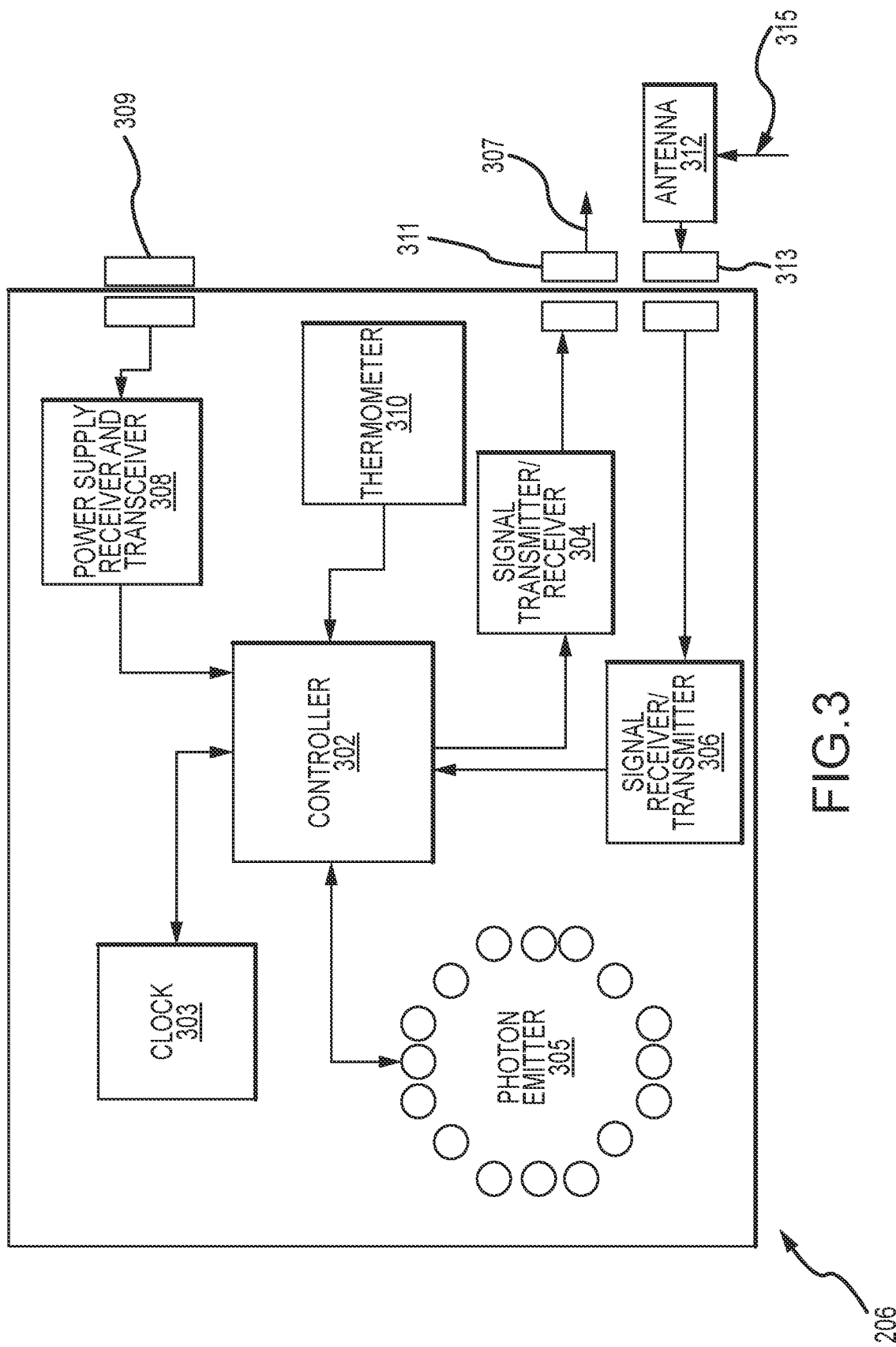
FIG. 3 is an example diagram of an LED light.

FIG. 3 provides a schematic of an LED light of the present disclosure 206. As shown in FIG. 3, the LED light 206 may comprise but is not limited to a controller 302, a clock generating crystal circuitry 303, wired signal transmitter/receiver 304, one or more photon emitters 305, a wireless signal receiver/transmitter 306, power supply and signal transmitter/receiver 308 and temperature sensor 310. Several bus communication infrastructures may be used with the disclosure provided herein, as will be understood by one skilled in the art, including, but is not limited to unidirectional, receiver, transceiver, omnidirectional and bidirectional. The synchronization of each LED light 206 in an LED light array is based on calculating and adjusting the difference from internal clock 303 and one or more of the other incoming master clock or incoming clocks of other LED lights 206. The master clock controller or other LED lights 206 send a signal 315 that is received by the LED light wireless signal receiver/transmitter 306, the wired signal transmitter/receiver 304 or wired power transmitter/receiver 308 containing the time of the master's internal clock and the timing the signal was sent or the timing of the adjusted clock from other LED lights 206. Each LED light 206 receives the signal through the signal receiver/transceiver 304, 306 or 308, where the information in the signal is transmitted to the controller 302. The controller 302 of the LED light 206 is in communication with the LED lights internal clock 303 and compares the time of the master clock with the time of the LED light's internal clock 303 and the time the signal was received. This allows the LED lights of an array to stay in synchronization with a limited drift up to 2.0 ns. While a drift of two nanoseconds is provided as an example, it will be understood by one skilled in the art that the synchronization of the master clock and the internal clock and the allowable timing drift can vary based on the communication type used and needs and application of the lighting system and may range from 100 ps, 500 ps, 750 ps, 1.0 ns, to 5 ns, 10 ns, 25 ns, 50 ns, 5 us, 10 us, 100 us, 500 us, 4 ms, 58 ms, 1000 ms, 2000 ms, 3000 ms, 4000 ms and all integers in between. The timing signal is broadcast by the master and the timing of each LED light is based on correlation of the timing signal from the master and the clock of the LED light. When timing is off, the LED light can produce feedback that indicates missing synchronization between the master and the LED light. LED light 206 may also send a wireless output signal 307 with various information about the LED light 206 such as the LED light's current time and the temperature of the LED light which may be sent to the master that the LED light is paired with, a gateway or other LED lights in the array. The LED light may also have a temperature sensor 310 and/or barometer in communication with the controller 302 that monitors the temperature and barometric pressure around the LED light or its environment.

The power supply 308 is in communication with and is operably coupled to the controller 302 and provides power to the LED light. A variety of power supplies may be used, depending on the scope and type of LED light, as will be understood by one skilled in the art, including AC, DC, batteries such as (12 volt and 9 volt). In the event of an AC or DC wired power supply, that power supply can also act as a receiver/transceiver for accepting and sending communication of clock timing and other signals.

Temperature and changes in barometric pressure can also have an impact signal communication between gateways, masters and LED lights leading to temperature clock drift and in the case of wireless communication signal frequency drift, which can cause issues in harmonics and missed communications between the LED light and the master, the master and Gateway and between LED lights. LED lights and masters can be recalibrated at repetitive internals as needed, such as every five minutes, one minute, 10 minutes, 30 minutes, one hour and every 24 hours, to account for changes in clock drift, temperature, pressure, and frequency drift to ensure that frequency drifts are not so large as to cause communications to fail. Monitoring and controlling the intestines of each LED light independently in a commercial install is critical to maintain signal frequency.

Changing the intensity of the pulsed photon emission of an LED light can achieve the desired response in the organism. For example, if you have a couple LED lights in an array that are hung under a vent for heating and air conditioning (HVAC) are closer to the organism than other lights in the array, then the LED lights under HVAC will need a lower photon emission intensity to even out the emission of the LED lights in the array.

The embodiment of system herein sends not only timing information in the communication system or signal but unique identification of each component within the communication signal and the deployed channel that the component should listen and send information on. The components of the system can communicate on discrete radio channels. The channels can be bidirectional communication, or a channel can be reserved for one direction such as in a transmit or receive only configuration. Each facility where the LED lights are deployed with wireless communication will have its own unique structures and design which can also create signal reflections and echoing characteristics. The method of synchronization as described herein is designed to consider echoes and reflections in a facility. By way example, the broadcast master's clock signal contains a timing of 1, 2, 3, 4, 5, 6, 7, 8, 9, 10 or 1 to 5, or 1 to 20 or as necessary for the timing of the system. If an LED light or sensors receives a signal from the master, gateway, or other LED lights where a number is out of order or repeats, such as the number 9 comes after 10, or number 9 repeats more than once then the LED light receiving the signal knows that the signal bounced off a wall, so the LED light received it twice or there is an error and to ignore the signal. If the signal timing goes 8 to 10 then you know a signal was missed. The unique identification and pairing of channels allow the components of the system to ignore communication signals that are not directed to it or does not belong to the system.

Several clocks or timing mechanisms may be used with the disclosure provided herein. By way of example, clock generating crystal circuitry such as a crystal oscillator or a quartz crystal oscillator may be used with the disclosure provided herein. A crystal oscillator is an electronic oscillator circuit that uses the mechanical resonance of a vibrating crystal of piezoelectric material to create an electrical signal with a constant frequency. This frequency is used to keep track of time and provides a stable clock signal for digital integrated circuit. In addition, resistor-capacitor circuits and microcontrollers may also be used for timing.

As used herein a wireless network is a computer network that uses wireless data connections between network nodes. Wireless networking is a method by which homes, telecommunications networks and business installations avoid the costly process of introducing cables into a building, or as a connection between various equipment locations. Wireless telecommunications networks are generally implemented and administered using radio communication. This implementation takes place at the physical level (layer) of the OSI model network structure. Examples of wireless networks include cell phone network, wireless local area networks (WLANs), wireless sensor networks, satellite communication networks, terrestrial microwave networks, ultra-wide band, RF, Bluetooth, ZigBee and mesh networks.

As used herein a mesh network (or simply meshnet) is a local network topology in which the infrastructure nodes (i.e., bridges, switches, and other infrastructure devices) connect directly, dynamically, and non-hierarchically to as many other nodes as possible and cooperate with one another to efficiently route data from/to clients. This lack of dependency on one node allows for every node to participate in the relay of information. Mesh networks dynamically self-organize and self-configure, which can reduce installation overhead. The ability to self-configure enables dynamic distribution of workloads, particularly in the event that a few nodes should fail. This in turn contributes to fault-tolerance and reduced maintenance costs As used herein, "duty cycle" is the length of time it takes for a device to go through a complete ON/OFF cycle or photon signal. Duty cycle is the percent of time that an entity spends in an active state as a fraction of the total time under consideration. The term duty cycle is often used pertaining to electrical devices, such as switching power supplies. In an electrical device, a 60% duty cycle means the power is on 60% of the time and off 40% of the time. An example duty cycle of the present disclosure may range from 0.01% to 90% including all integers in between.

As used herein "frequency" is the number of occurrences of a repeating event per unit time and any frequency that may be used in the system of the present disclosure. Frequency may also refer to a temporal frequency. The repeated period is the duration of one cycle in a repeating event, so the period is the reciprocal of the frequency.

As used herein, the term "waveform" refers to the shape of a graph of the varying quantity against time or distance.

Figure 10:
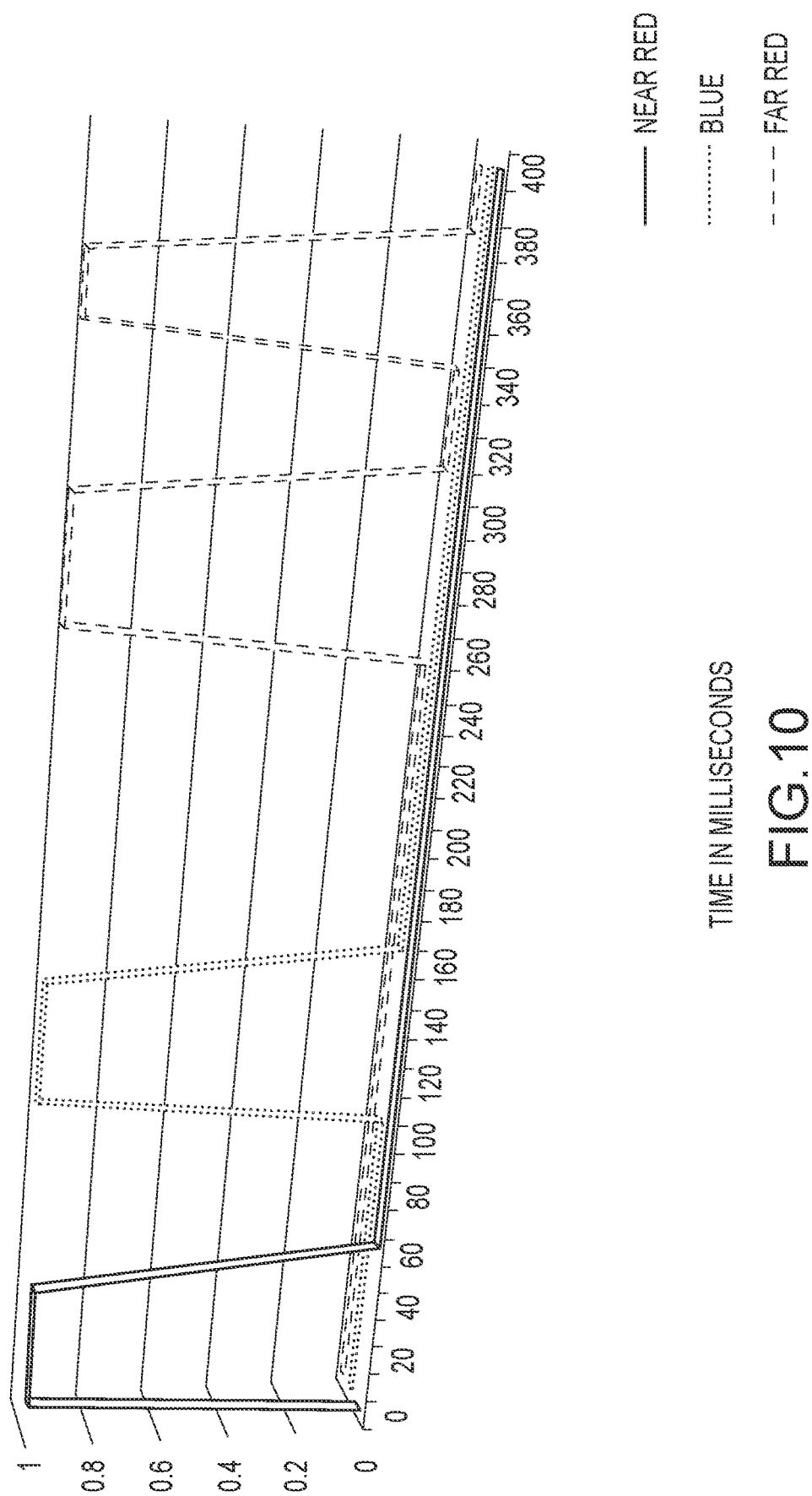
FIG. 10 is an example of a photon recipe with three components and the recipe step starting at 0 milliseconds.

As used herein, the term "pulse wave" or "pulse train" is a kind of non-sinusoidal waveform that is similar to a square wave, but does not have the symmetrical shape associated with a perfect square wave. An example is shown in FIG. 10 where a photon recipe is shown with three components with various pulse waves or trains, with a recipe step in milliseconds and going from 0 to 440 ms. It is a term common to synthesizer programming and is a typical waveform available on many synthesizers. The exact shape of the wave is determined by the duty cycle of the oscillator. In many synthesizers, the duty cycle can be modulated (sometimes called pulse-width modulation) for a more dynamic timbre. The pulse wave is also known as the rectangular wave, the periodic version of the rectangular function.

As used herein, the term "offset" means a ON duration of a pulse that is initiated at a different timing from the ON duration of another pulse. By way of example a first photon pulse may be initiated at the start of a repetitive cycle or duty cycle with a second or more other photon pulses.

As used herein, Radio-frequency identification (RFID) uses electromagnetic fields to automatically identify and track tags attached to objects. The tags contain electronically stored information. Passive tags collect energy from a nearby RFID reader's interrogating radio waves. Active tags have a local power source (such as a battery) and may operate hundreds of meters from the RFID reader. Unlike a barcode, the tag need not be within the line of sight of the reader, so it may be embedded in the tracked object. RFID is one method of automatic identification and data capture (AIDC).

As used herein, Ethernet, is a family of computer networking technologies commonly used in local area networks (LAN), metropolitan area networks (MAN) and wide area networks (WAN).[1] It was commercially introduced in 1980 and first standardized in 1983 as IEEE 802.3, and has since retained a good deal of backward compatibility and been refined to support higher bit rates and longer link distances. Over time, Ethernet has largely replaced competing wired LAN technologies such as Token Ring, FDDI and ARCNET.

As used herein, "bluetooth" is a wireless technology standard for exchanging data between fixed and mobile devices over short distances using short-wavelength UHF radio waves in the industrial, scientific and medical radio bands, from 2.400 to 2.485 GHz, and building personal area networks (PANs). It was originally conceived as a wireless alternative to RS-232 data cables.

As used herein, "Zigbee" is an IEEE 802.15.4-based specification for a suite of high-level communication protocols used to create personal area networks with small, low-power digital radios, such as for home automation, medical device data collection, and other low-power low-bandwidth needs, designed for small scale projects which need wireless connection. Hence, Zigbee is a low-power, low data rate, and close proximity (i.e., personal area) wireless ad hoc network.

Commissioning LED Light Array with a Master and/or Gateway

Figure 4:
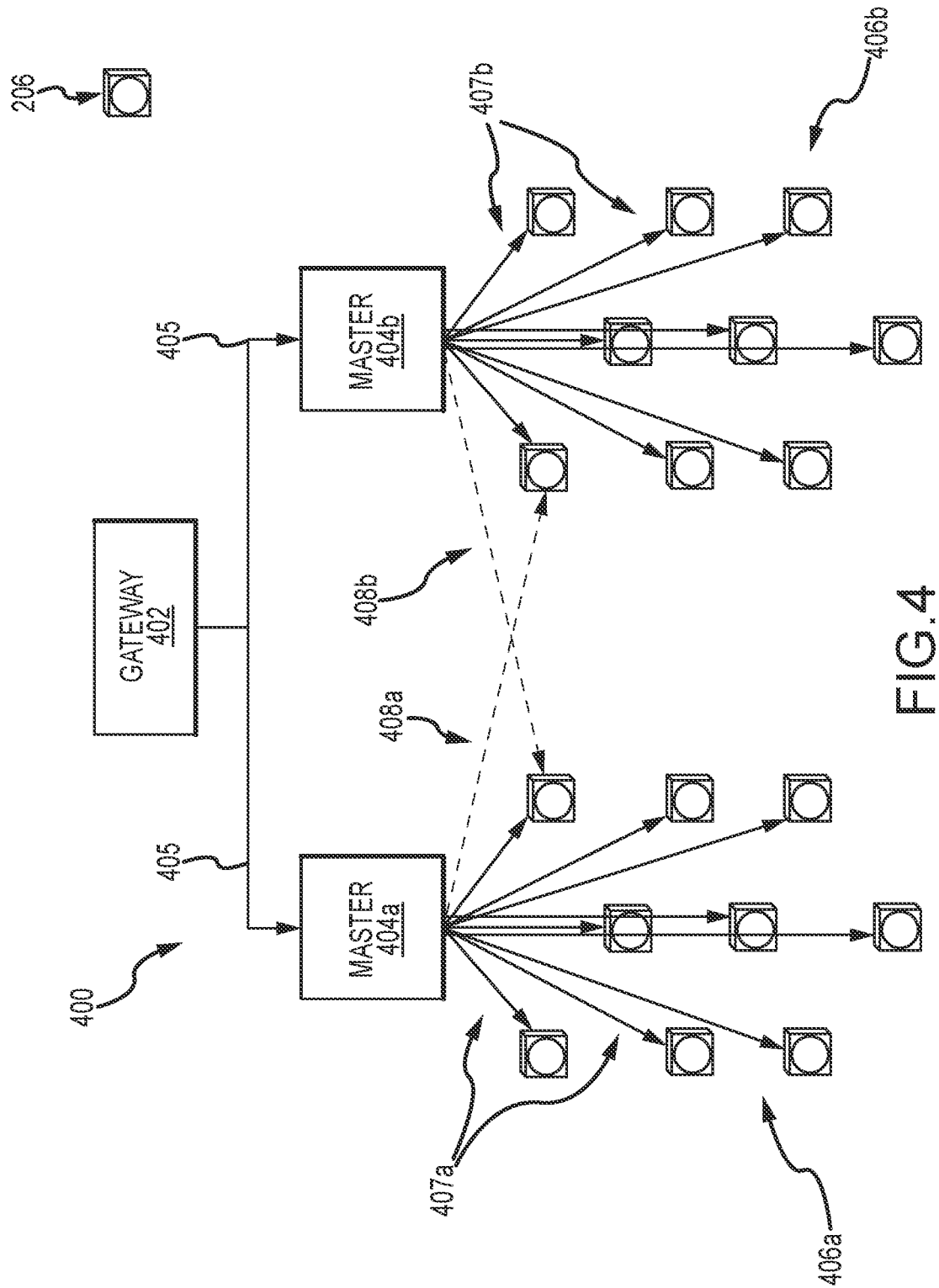
FIG. 4 is an example diagram showing the synchronization of an LED light.

The system provided herein allows for the commissioning of a systems of LED lights in an array with a master and/or gateway by allowing the LED lights to choose the master and/or gateway to pair with that has the best communication connection or to allow the master and/or gateway to choose which LED lights to pair with that have the best communication connection. As shown in FIG. 4, a Gateway 402 is hardwired 405 to two (2) masters 404a and 404b. Each master 404a and 404b is then in communication by wireless signal with an array of nine (9) LED lights 406. The first master 404a sends a signal to each LED light 206, the LED light receives the signal from the master 404a and responds with a signal of its own indicating the signal has been received. Then the second master 404b sends a signal to the same LED light 206. The LED light will then analyze the signal from the second master 404b and will then choose which master is in best communications and commission itself as a pair to that master.

As shown in FIG. 4, in the commissioning process, LED light array A (406a) has received wireless signals 407a from the first master 404a and wireless signals 408b from the second master 404b. Based on the signal strength and quality of communication, the LED lights 206 of LED light Array A 406a rank the first master 404a as the preferred master and asks to pair with the first master 404a. The LED lights 206 of LED light Array B 406b rank the second master 404b as the preferred master and asks to pair with the master 404b. The master 404a and master 404b can also compare the communications between said LED light 206 and communicate through the gateway to make a choice on which master has the best communication with LED light 206 and choose which master commissions itself as a pair with LED light 206. Please note that the commissioning process can also be in the opposite direction with the LED light sending a signal to the master and based on the signal strength the master may request to pair with a specific LED light.

The system can also be set up to use the LED lights to indicate during the commissioning of the LED light system set up to indicate signal strength. Different colors from each LED light can be used to indicate the strength of the signal communication between the LED light in relation to a master (based on two-way communication between master and LED light). This allows for installers to visually place each LED light and to quickly move the LED lights or pairing to the location or master and/or gateway with the strongest signal, the intensity of the signal and the data contained within the signal, i.e., the stronger the intensity of the signal received by the emitter, the closer the unit is to the LED light. In an additional embodiment, each LED light may send signals to other LED lights in an array with information regarding the intensity of the signal or data within being received or the LED light may communicate directly with a master or gateway regarding the information in data signal (such as in the case of an emergency signal from a mobile real time location unit), thus allowing the LED lights to triangulate the exact location of the unit within the lighting array and to adjust their photon signals as appropriate. LED lights can be programed with one or more signals which facilitates a change in light emission recipes or can received signals from a gateway with such commands.

In an implementation of the current system utilizing wireless communication, a variety of devices have the capability of producing signal or harmonics that have the capability of interfering with the communication amongst LED lights, masters, and gateways. This issue can be mitigated by using specific channels with limited frequency range, thus providing a signal with a very narrow profile that is distinguishable by paired components.

Figure 5:
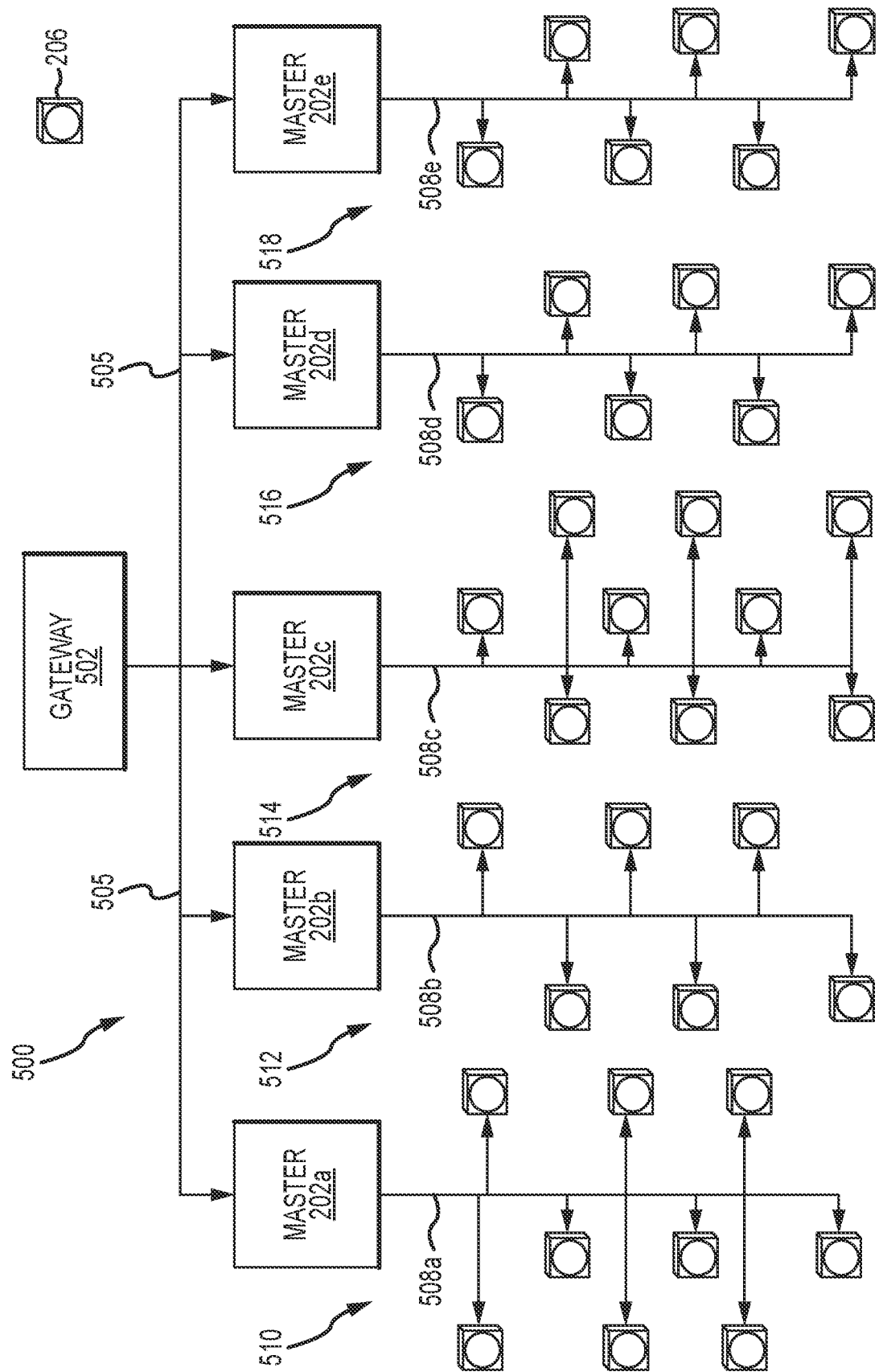
FIG. 5 is an example diagram showing the synchronization of LED light arrays that are hardwired with a series of masters and a gateway.

FIG. 5 shows an example of a gateway in communication with and control of five masters 202a, 202b, 202c, 202d, and 202e, where each master is in communication with two or more LED lights 206 and where each LED light contains at least one photon emitters in communication. In this example, a Gateway 502 is hardwired by Ethernet 505 and is in communication and provides commands and control of each Master 202a, 202b, 202c, 202d, and 202e. The gateway 502 also provides communications to third parties, such as through the internet or with a hardwired CPU, allowing two-way monitoring and control activities with third the Pulsed LED lighting array as needed. As will be understood by one skilled in the art, the number of masters 202a, 202b, 202c, 202d, and 202e in communication and under the control of one gateway 502 may range from 2, 3, 5, 9, 13, 17, 24, 29, 33, 42, 79, 104, 200, 400, 650, 1000, 15000 and all integers in between.

Each master 202a, 202b, 202c, 202d, and 202e in turn, is in communication and provides control of two or more LED lights 206 in an array 510, 512, 514, 516, and 518. In FIG. 5, each master 202a, 202b, 202c, 202d, and 202e is in communication and control of arrays 510, 512, 514, 516, and 518 of between six and nine LED lights. As will be understood by one skilled in the art, the number of LED lights 206 in an array in communication with each master 604 may range from 2, 3, 5, 9, 13, 18, 22, 49, 63, 74, 121, 205, 360, 6400, 1100, 15001 and all integers in between.

In FIG. 5, each master 202a, 202b, 202c, 202d, and 202e is hardwired 508a, 508b, 508c, 508d, 508e to each individual LED light 206 within an array 510, 512, 514, 516, and 518. The hardwire may be of any type of wiring that provides for a communication architecture to allow for multiple signals of information to be bi-directionally transmitted through the wire.

In FIG. 5, five masters 202a, 202b, 202c, 202d, and 202e are shown with each master paired with an LED light array 510, 512, 514, 516, and 518. Each master has control and pairing with a specific array allowing each individual array to have its own photon emission pattern, with its own recipes and synchronization. By way of example, master 202a is paired with LED light array 510 which may be an array that is in a poultry facility and is designed to emit photons in a synchronized emission to induce young birds to eat and grow without inducing sexual maturity. Master 202b is paired with an LED light array 512 that may be synchronized to emit photons to induce sexual maturity in birds for egg production, while masters 202c and 202d may be in an area of a facility that is dedicated to dairy cattle with LED light arrays 514 and 516 synchronized to emit photon to encourage milk production while master 202e is paired with LED light array 508e that is an area of the facility that is temporarily used for administration of the facility and the LED light array 518 is emitting regular white light. Please note that in a wired solution, a master clock can be sent on a communication bus that is simply a repetitive signal that the LED light uses to cadence the photon emission recipe in the LED light. In this case the LED lamp does not need to have an internal clock of its own. Further the system provided herein also allows for the synchronization of timing between gateway and master as well as having the master controller change its timing to match an average of the of LED light clocks.

Figure 6:
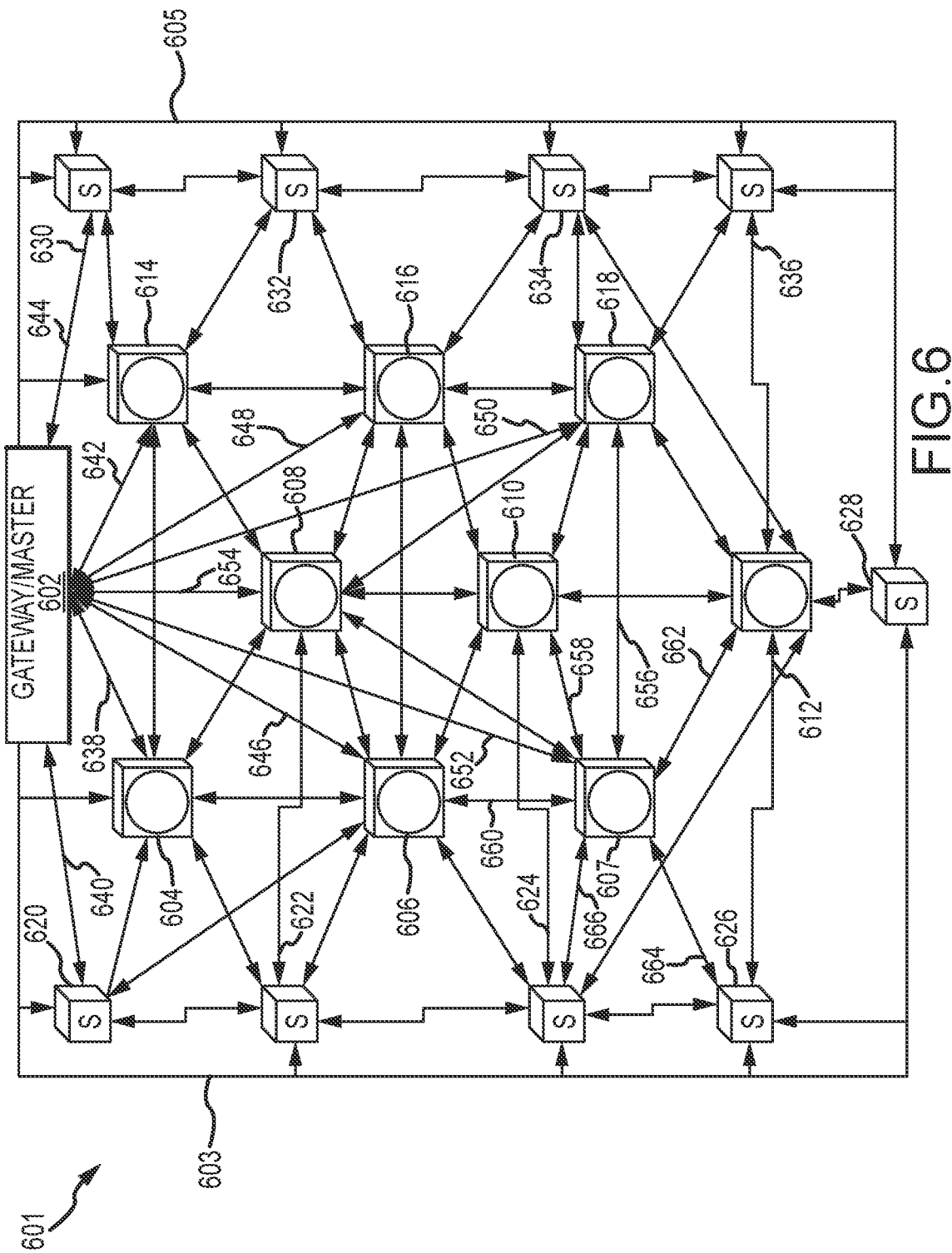
FIG. 6 is an example diagram showing the synchronization of LED light arrays that are in wireless communication with a gateway or master.

FIG. 6 provides an example of synchronization of a gateway/master with an array of LED lights where each LED light contains at least one photon emitter, 600. In this example, through the use of a master clock within the gateway which is compared with an internal clock within each LED light, each gateway/master is able to maintain synchronous timing and control of each LED light and sensor within the array.

As shown in FIG. 6, a gateway/master 602 is provided in wireless communication with an array of LED lights and sensors 601. In this example, no masters are provided and the gateway 602 provides control and communication to the outside world as well as the ability to update firmware, photon emission recipes, and intensity setting for the LED lights. The Gateway also can initiate 24-hour clock timing of how many hours per day the LED lights are on and off during the day. The Gateway initiates the synchronization master clock that is wirelessly broadcast to the LED lights for the synchronization of emission of photons or light from the LED lights within the array as well as for the synchronization light and communication with the sensors within the array. As will be understood by one skilled in the art a variety of gateway/masters may be used, such as solid-state circuit with digital output control or a central processing unit (CPU), provided the device is capable of control (input/output of the parameters and the appropriate instructions or the specialized functions for the modulation of photons) and communication to the photon emitters in the array and sensors as well as receiving communications from these devices.

As discussed above, the synchronization of each LED light in the array is achieved through the use of a master clock within the gateway. By way of example, at a known repetitive rate, the gateway 602 broadcast a signal to the LED light array. Each LED light in the array can then also respond back to the gateway 602 with individualized data 603, 605, 638, 640, 642, 644, 646, 648, 650, 652 and 654 to each LED light and sensor 604, 606, 607, 608, 612, 614, 616, 618, 620, 622, 624, 626, 628, 630, 632, 634, 636 within the array. The signal contains information for each LED light and sensor such as emission recipe commands and firmware commands, but also contains the timing of the master clock and the time the signal was sent by the gateway. Each LED light receives the signal and reads the timing of the time of the master clock as well as the time the clock was sent. This allows each LED light as well as each sensor to compare the time of the master clock with its internal clock and determine if the internal clock is off from the timing of the master clock, and if so, by how much. This allows the LED light to recalibrate the time of its internal clock and to synchronize the photon emissions within the LED light to the gateway master clock.

In another embodiment of the current disclosure, each LED light that has received the master clock signal 604, 606, 607, 608, 614, 616, and 618 will then at a secondary known time, will send an output signal with its own internal clock to one or more LED lights in the array. This is shown in FIG. 6 with LED light 607 sending signals 656, 658, 660, 662, 664 and 666 with its internal clock, which is sent to LED lights 606, 608, 610, and 612 and sensors 624 and 626. At the same time LED light 607 is also receiving internal clock signals from LED lights 606, 608, 610 and 612, allowing the LED light 607 to refine its clock drift and its internal clock. For the master clock of the gateway, at a known repetitive rate (by way of example 800 ps, 1 us, 50 μ, as well as 5 μs, 10 μs, 12 μs, 25 μs, 100 μs, 500 μs and 1000 μs) sends its timing signal to the LED lights and sensors within in the array.

Also provided in FIG. 6 and shown in FIG. 5 is an array of least two photon emitters 604, 606, 606, 608, 610, 612, 614, 616 and 618 and/or sensors 620, 622, 624, 626, 630, 632, 634, and 636 in communication with the gateway 602. As with the gateway 602, each LED light and /or sensor has an internal clock. Each photon emitter and/or sensor is capable of receiving the master clock signal from said gateway and master controller as well as photon signals from other photon emitters or sensors in the array. This allows each emitter and sensor in the array to triangulate and know the location of the other sensors and emitters in the array as well as what those emitters and sensors are doing. Each photon emitter and each sensor are capable of generating its own master clock signal transmitting the time of the photon emitter's internal clock.

Each LED light and sensor in the array are also capable of generating an output signal with the time of the internal clock of that emitter or sensor. The output signal is transmitted to the master controller as well as to the other LED lights and sensors in the array. Each LED light and sensor will also receive signals from other LED lights and sensors within the array, allowing each LED light and sensor to be synchronized with other LED lights. Each LED light can receive adjusted clock signals from many other LED lights and sensors in the array and use clock adjustments along with others to create a more sophisticated and accurate clock adjustment. The meshing of this bidirectional communication by utilizing communication through multiple pathways between many LED lights and sensors in the array, the system has better communication pathways and can extend those pathways for long distances away from the gateway 602. By utilizing unique identification within the communication for each LED light and sensor in the array, firmware updates, photon modulation recipes, timing and other information can now be sent to all LED lights and sensors in the array. This allows buildings or facilities with several thousand LED lights and sensors to communicate efficiently and stably over large distances and through many floors or levels within the buildings or agricultural feed lots.

Figure 9:
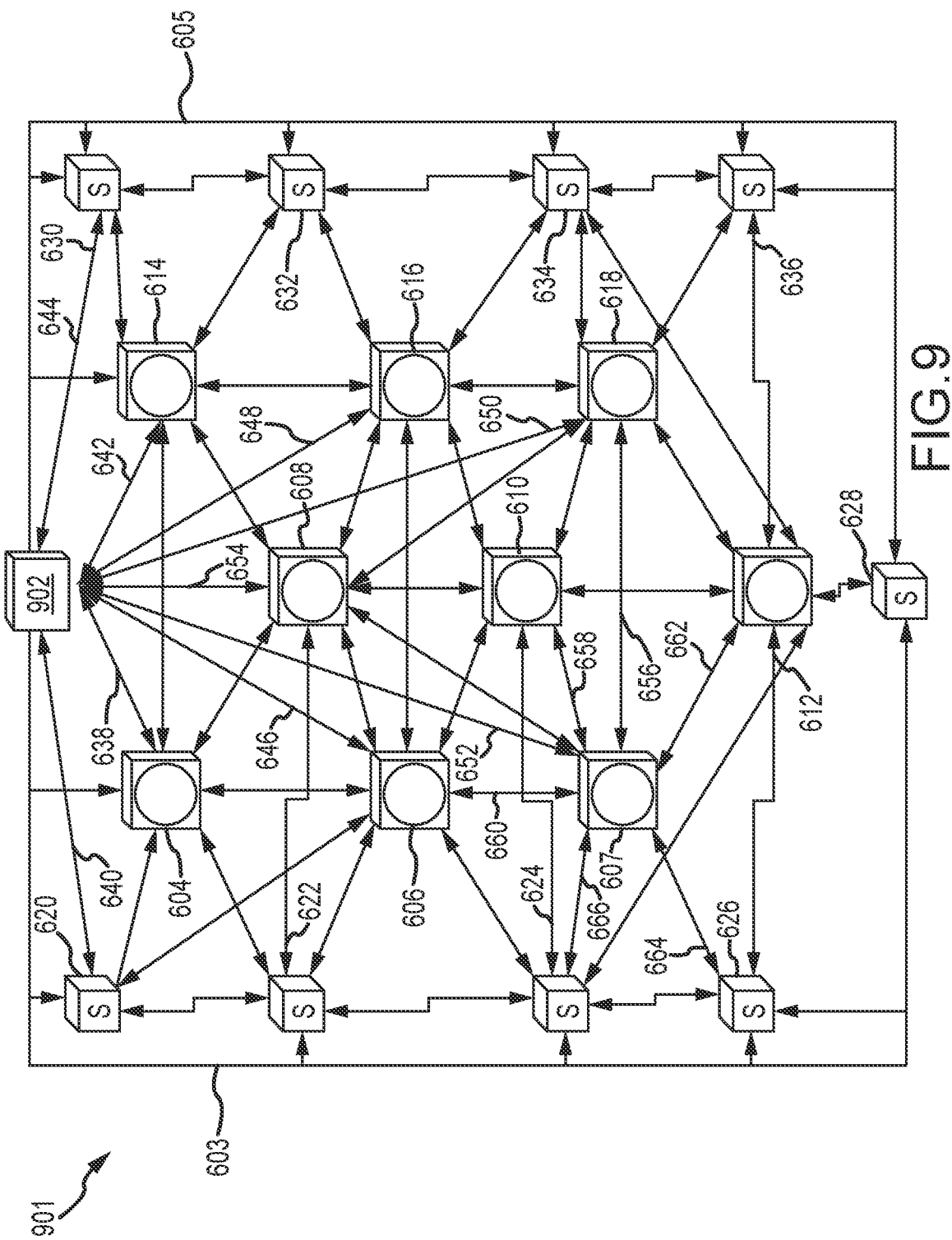
FIG. 9 is an example diagram showing the synchronization of LED light arrays that are in wireless communication where a single LED is acting as a gateway or master.

FIG. 9 provides an example of synchronization of an array of LED lights where an LED light 902 act as either a gateway or a master, 901. In this example, and as discussed ini reference to FIG. 6, through the use of a master clock within the LED light which is compared with an internal clock within each LED light, the LED light that is acting as a gateway/master is able maintain synchronous timing and control of each LED light and sensor within the array.

The present disclosure also provides for the synchronizing the pulsing or modulation of photon emission from two or more LED lights within an LED light array within a mesh network protocol. Each LED Light in the mesh network broadcasts and receives clock signals from other LED lights in the system, where each LED light performs a calculation of the average time of the LED lights in the array the LED is in communication with to best align its internal clock to the other received clocks within the LED light array. The LED light then broadcasts its adjusted clock to other LED lights within the array, where over repeated cycles the clocks of all LED lights converge or align with each other.

The present disclosure also provides for the synchronizing the pulsing or modulation of photon emission from two or more LED lights within an LED light array within a mesh network protocol. Wherein some LED Lights are parent lights in the mesh network that are responsible to maintaining clocks and broadcast their clocks timing to child LED lights in the system, creating a hierarchy of LED lights with parent LED lights maintain the timing of the array and child LED lights simply listening and responding to the parents.

A variety of sensors may be incorporated into the system described herein in order to provide various information about the system as well as the organisms associated with the system in the facility. A sensor can not only sense information but can also send control information to $3^{rd}$ party or external systems such as feed conveyors and watering systems. Examples of such sensors may include but are not limited to temperature sensors, smoke, moisture, barometers, stem diameter, GPS, accelerometers, heart rate, blood pressure, ovulation, hormone tracking, such as pheromones, estrogen, testosterone, and cortisol (which may be used to monitor stress), vibration, sound and vocalization to list of measurements, as well as $3^{rd}$ party sensors such as egg counters, feed sensors, and weight.

Data collected by the sensor can be relayed to a controller where the modulation of photon from LED lights in an array can be adjusted or changed. For example, based upon weight scales in a commercial egg laying facility, the weight of a sample of birds can be collected and sent to the LED lighting system where the modulation recipe can be adjusted as needed. In the case where the weight of the birds is too low, the intensity of the recipe can be increased to increase their desire to eat and thus add weight to the birds. In the case where the birds' weight is too high, the intensity of the led lighting system can be decreased thus decreasing the birds desire to eat and reduce the weight of the birds. Traditionally this control is performed by increasing or decreasing the temperature in the chicken barns. However, if you increase the temperature you can decrease the desire of the birds to eat and thus slow down their consumption rate. You can also decrease the temperature in the barns and increase the desire of the bird to eat thus increasing consumption of the birds. Adjusting the intensity of the lights is a more economically viable solution and can have more incremental control than adjusting the temperature in a barn.

The modulation of the emission of photons or light from an LED light and an LED light array to an organism, can stimulate or influence a variety of desired biological responses or functions, including but not limited to, fertility, ovulation, hunger, egg production, sexual maturity, milk production, hormone production, behavior and socialization, root, tissue or hyphal growth, vegetative growth, flower or fruiting body production, fruit, spore or seed production, stopping growth, elongation of a specific plant part, repairing an organism or destruction of the organism and interpolation of circadian inputs. Examples include but are not limited to; creating a signal with one, two or more components of electro-magnetic wave emission pulse trains (photons or light) of individual color spectrums in sufficient intensity to drive photochemical response in an organism to control a desired biological function, using the relationship between the timing of ON durations of at least two components within a repetitive signal. Specifically, by providing a signal with one or multiple repetitive photons or light pulses at specific combination of rates relative to the timing of the ON duration of each component, including intensities, waveforms, photochemical responses by organisms can be stimulated and optimized and adjusted controlled or determined manner.

Examples of organisms may include, but is not limited to, humans, ungulates, including but not limited to cattle, horses, camels, pigs, deer, elk, alpacas, lamas, and moose, carnivores, including but not limited to bears, the weasel family, dogs, cats, wolves, lions, tigers, skunks, rodents, including but not limited to rats, mice, and beaver, chiropteras, including but not limited to bats, marsupials, including but not limited to kangaroos and opossums and cetacean, including, whales and dolphins, chickens, grouse, quail, pheasant, quail, parrots, water fowl, geese, swans, doves, organisms of prey, song organisms, turkey, owls, vultures, penguins, humming birds, ostrich, duck, mollusks, such as clams, oysters, octopuses, squid, snails; arthropods such as millipedes, centipedes, insects, spiders, scorpions, crabs, lobsters, shrimp; annelids, such as earthworms and leeches; sponges; and jellyfish, microorganisms, algae, bacteria, fungi, gymnosperms, angiosperms and pteridophytes, citrus, table grapes, wine grapes, bananas, papaya, *Cannabis* sp., coffee, goji berries, figs, avocados, guava, pineapple, raspberries, blueberries, olives, pistachios, pomegranate, artichokes and almonds; vegetables such as artichokes, asparagus, bean, beets, broccoli, Brussel sprouts, Chinese cabbage, head cabbage, mustard cabbage, cantaloupe, carrots, cauliflower, celery, chicory, collard greens, cucumbers, daikon, eggplant, endive, garlic, herbs, honey dew melons, kale, lettuce (head, leaf, romaine), mustard greens, okra, onions (dry & green), parsley, peas (sugar, snow, green, black-eyed, crowder, etc.), peppers (bell, chile), pimento, pumpkin, radish, rhubarb, spinach, squash, sweet corn, tomatoes, turnips, turnip greens, watercress, and watermelons; flowering type bedding plants, including, but not limited to, *Ageratum, Alyssum, Begonia, Celosia, Coleus*, dusty miller, *Fuchsia, Gazania*, Geraniums, gerbera daisy, Impatiens, Marigold, *Nicotiana*, pansy/*Viola, Petunia, Portulaca, Salvia*, Snapdragon, Verbena, *Vinca*, and Zinnia; potted flowering plants including, but not limited to, African violet, *Alstroemeria, Anthurium, Azalea, Begonia, Bromeliad, Chrysanthemum, Cineraria, Cyclamen*, Daffodil/Narcissus, Exacum, Gardenia, Gloxinia, Hibiscus, Hyacinth, Hydrangea, Kalanchoe, Lily, Orchid, Poinsettia, Primula, regal pelargonium, rose, tulip, *Zygocactus/Schlumbergera*; foliage plants including, but not limited to, *Aglaonema, Anthurium, Bromeliad, Opuntia*, cacti and succulents, Croton, *Dieffenbachia, Dracaena, Epipremnum*, ferns, ficus, Hedera (Ivy), *Maranta/Calathea*, palms, *Philodendron, Schefflera, Spathiphyllum*, and *Syngonium*. cut flowers including, but not limited to, *Alstroemeria, Anthurium*, Aster, bird of paradise/Strelitzia, calla lily, carnation, *Chrysanthemum*, Daffodil/Narcissus, daisy, Delphinium, Freesia, gerbera daisy, ginger, Gladiolus, Godetia, Gypsophila, heather, iris, Leptospermum, Liatris, lily, Limonium, Lisianthus, Orchid, Protea, Rose, Statice, Stephanotis, Stock, Sunflower, Tulip; cut cultivated greens including, but not limited to, plumosus, tree fern, boxwood, soniferous greens, Cordyline, Eucalyptus, hedera/Ivy, holly, leatherleaf ferns, Liriope/Lilyturf, Myrtle, Pittosporum, Podocarpus; deciduous shade trees including, but not limited to, ash, birch, honey locust, linden, maple, oak, poplar, sweet gum, and willow; deciduous flowering trees including, but not limited to, Amelanchier, callery pea, crabapple, crapemyrtle, dogwood, flowering cherry, flowering plum, golden rain, hawthorn, Magnolia, and redbud; broadleaf evergreens including, but not limited to, Azalea, cotoneaster, Euonymus, holly, Magnolia, Pieris, Privet, Rhododendron, and Viburnum; coniferous evergreens including, but not limited to, Arborvitae, cedar, cypress, fir, hemlock, juniper, pine, spruce, yew; deciduous shrubs and other ornamentals including, but not limited to, buddleia, hibiscus, lilac, *Spirea*, Viburnum, *Weigela*, ground cover, bougainvillea, clematis and other climbing vines, and landscape palms; fruit and nut plants including, but not limited to, citrus and subtropical fruit trees, deciduous fruit and nut trees, grapevines, strawberry plants, other small fruit plants, other fruit and nut trees; cut fresh, strawberries, wildflowers, transplants for commercial production, and aquatic plants; pteridophyte plants including, but not limited to ferns and fungi including but not limited to basidiomycetes, ascomycetes, and sacchromycetes. The system of the present disclosure provides a photon pulse for both C3 and C4 photosystems as well as "CAM" plants (Crassulacean acid metabolism), cyanobacteria or eukaryotic green algae or other organisms.

The modulation or pulsing of photons or light from an LED light to an organism, can stimulate or influence a variety of desired biological responses or functions, including but not limited to, fertility, ovulation, hunger, feed conversion, egg production, egg weight, egg shell quality, egg nutrients, egg weight distribution, sexual maturity, organism mass, milk production, hormone production, behavior and socialization, morphology, root, tissue or hyphal growth, vegetative growth, flower or fruiting body production, fruit, spore or seed production, stopping growth, elongation of a specific plant part, repairing an organism or destruction of the organism and interpolation of circadian inputs. Examples include but are not limited to; creating a signal with one, two or more components of electro-magnetic wave emission pulse trains (photons or light) of individual color spectrums in sufficient intensity to drive photochemical response in an organism to control a desired biological function, using the relationship between the timing of ON durations of at least two components within a repetitive signal. Specifically, by providing a signal with one or multiple repetitive photons or light pulses at specific combination of rates relative to the timing of the ON duration of each component, including intensities, waveforms, photochemical responses by organisms can be stimulated and optimized and adjusted controlled or determined manner.

When using one or more LED lights in artificial lighting systems, precise control over modulation of photon emission from the individual LED lights is vital to modifying biological reactions in organisms. If an organism is physically located under and exposed to the photon emissions of more than one LED light those photon emissions from each LED light must be highly synchronized to each other in order to reduce confusion and maximize effects in the biological change. The modulation of said photon emissions comes in the form of control over the matrix of when to turn any and all wavelengths ON or OFF and at what intensity to emit the photons. For the purposes of the present disclosure, this matrix will be referred to as a "Recipe". As listed in Table 1 below, each channel number can be controlled individually or in groups. By stitching Table 1 together over time, a waveform of the ("Recipe") is produced.

TABLE 1

| Channel # | Wavelength (nm) | Step 1 Duration (1) ms & Intensity | Step 2 Duration (1) ms & Intensity | Step 3 Duration (1) ms & Intensity |
|---|---|---|---|---|
| 1 | 445 | ON: 75% | ON: 80% | ON: 90% |
| 2 | 455 | OFF: 0% | ON: 75% | OFF: 0% |
| 3 | 465 | OFF: 0% | OFF: 0% | OFF: 0% |
| 4 | 395 | OFF: 0% | OFF: 0% | ON: 100% |
| 5 | 625 | OFF: 0% | OFF: 0% | OFF: 0% |
| 6 | 660 | ON: 100% | ON: 100% | ON: 100% |
| 7 | 740 | ON: 100% | OFF: 0% | OFF: 0% |
| 8 | 660 | ON: 50% | ON: 50% | ON: 50% |
| 9 | 500 | OFF: 0% | OFF: 0% | OFF: 0% |
| 10 | 365 | OFF: 0% | OFF: 0% | OFF: 0% |
| 11 | 500 | ON: 100% | ON: 50% | ON: 25% |
| 12 | 525 | OFF: 0% | ON: 0% | OFF: 0% |
| 13 | 592 | OFF: 0% | OFF: 0% | OFF: 0% |
| 14 | White Light | ON: 100% | ON: 100% | OFF: 0% |

The Recipe and the process of iterating through the individual steps must be synchronized between multiple LED lights in a system. For example, the Recipe can reside in any component in the system. If the system has a gateway or master the recipe can be stored in either component and transferred thought the bus communication to the LED lights and timing of the steps or groups of steps can be controlled from any device such as the gateway, master or LED lamps themselves. The gateway and master can also directly send channel by channel and step by step direct control to the lamps. The LED light can also contain the Recipe and use timing information from other Led lights, gateway or the master to synchronize the iterations through the steps or groups of steps in a recipe. All of which is the ultimate purpose to affect the synchronization and control of photon emissions from individual photon sources within a LED light and that of multiple LED lights.

Maximization of Power Efficiency in a Photon Array

Figure 7:
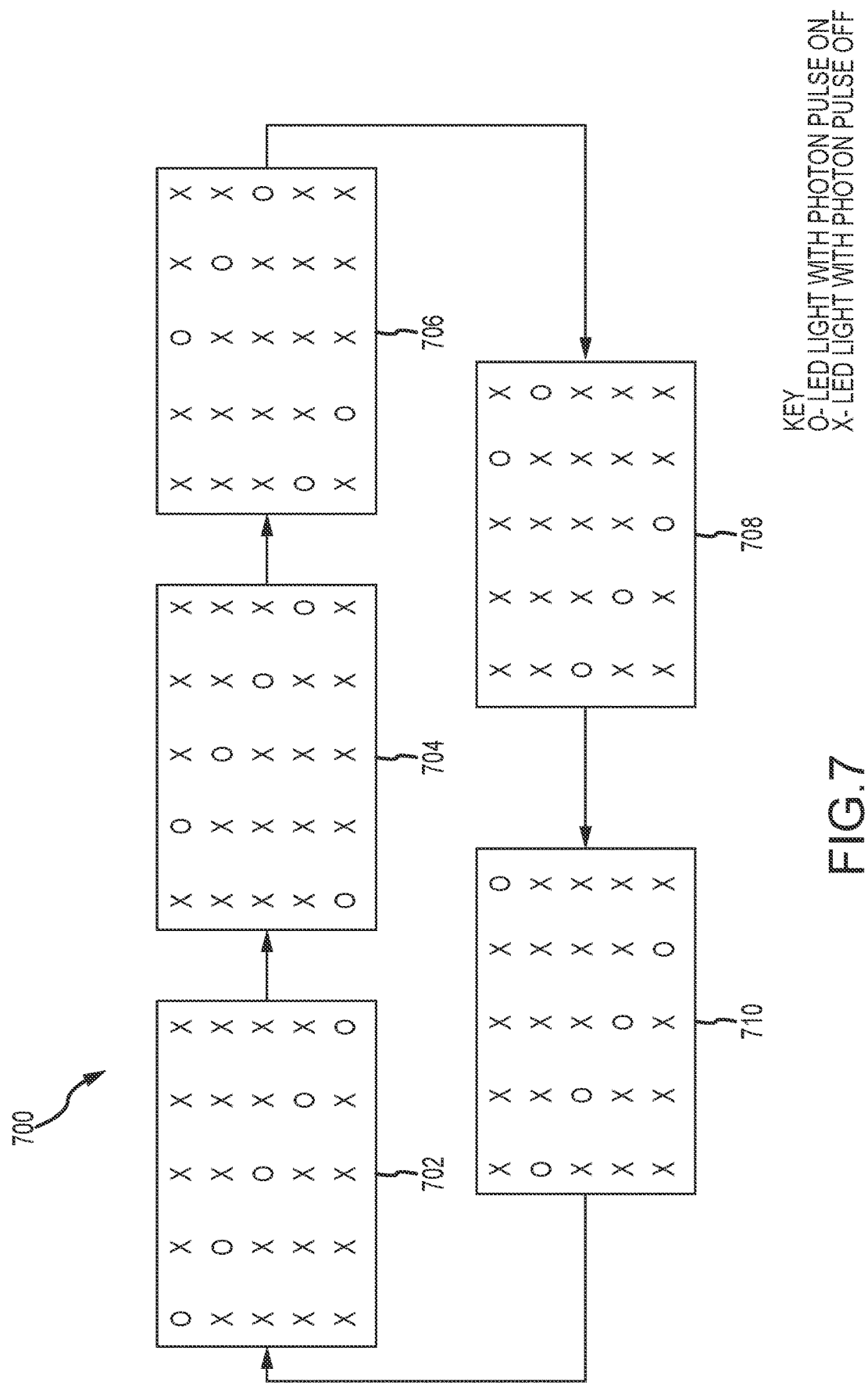
FIG. 7 is a diagram showing an example of synchronization of an array of 25 photon emission housing units to maximize power efficiency at 20%.

FIG. 7 provides an example of synchronization of an array of 25 LED lights to maximize power efficiency, using 20% power when compared to 100% power with all emitters ON. As shown in FIG. 7, a network array of 25 LED lights in a growing facility with 20% of the emitters ON and 80% OFF. Moving in a clockwise fashion, FIG. 7 provides a flow diagram of an array of 25 LED lights with five units in an ON cycle and 20 in an OFF cycle. Step 702 shows a network array of 25 LED lights with five units ON and pulsing photons. Step 704 shows a network array of 25 LED lights with the next 5 units ON and pulsing photons from those in the ON in 702. Step 706 shows a network array of 25 LED lights with the next five (5) units ON and pulsing photons from those in the ON in 704. Step 708 shows a network array of 25 LED lights with the next five (5) units ON and pulsing photons from those in the ON in 706. 710 shows a network array of 25 photon emission housing units with the next 5 units ON and pulsing photons from those in the ON in 708.

The timing and transition of LED lights from ON and OFF is, as discussed above, based on communications between a master and/or gateway with each LED light and the master clock of the mater/gateway and the internal clock within each LED light. The gateway/master will send a command to the emitters with a signal and based on the internal clock of each emitter and the command of the gateway, the emitters will go ON and OFF in order to have an even spread of emitters ON at a certain percentage (example being 20%) and a commensurate percentage OFF.

While FIG. 7 shows an array of 25 photon emitters, it will be understood by one skilled in the art that the array may encompass any number of emitters including 2, 3, 4, 6, 9, 10, 13, 20, 25, 50, 68, 74, 99, 100 1000, 2000, 5000, and 10000 and all integers in between, as will be understood. Further, while FIG. 7 shows an array using the method of the current disclosure to use 20% power when compared all of the emitters ON, it will be understood by one skilled light in the art that the method of the current disclosure can produce a range of power efficiencies from 1%, 5%, 10%, 20%. 50%, 75% and up to 99% depending on the size of the photon emitter array and the desired power usage for the array.

Figure 8:
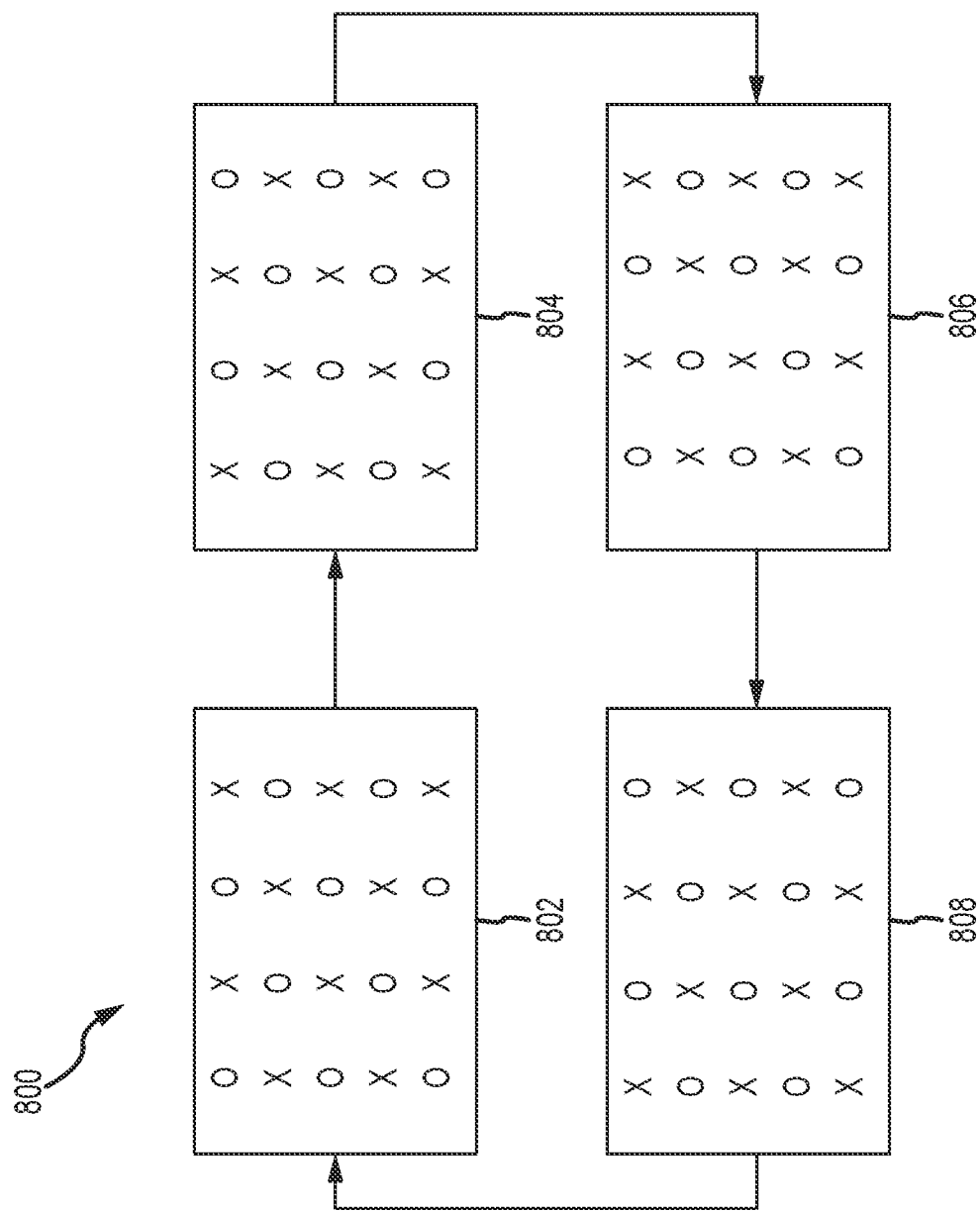
FIG. 8 is a diagram showing an example of synchronization of an array of 20 photon emission housing units to maximize power efficiency at 50%.

FIG. 8 provides a second example of synchronization of an array of 20 LED lights to maximize power efficiency, using 50% power with a shift of 10 LED lights ON while 10 LED lights are OFF. As shown in FIG. 8, a network array of 20 LED lights in a growing facility with 50% of the LED lights ON and 50% OFF. Moving in a clockwise fashion, FIG. 8 provides a flow diagram of an array of 20 LED lights with 10 units in an ON cycle and 10 in an OFF cycle to maximize power efficiency to reduce the power stress to the system, turning 10 units ON at once reduces power stress when compared to 10 at once. Step 802 shows a network array of 10 LED lights with 10 units ON and pulsing photons. Step 804 shows a network array of 20 LED lights with the opposite 10 units ON and pulsing photons from those in the ON in 802. Step 806 shows a network array of 20 LED lights with the opposite 10 units ON and pulsing photons from those in the ON in 804. Step 808 shows a network array of 20 LED lights with the opposite 10 units ON and pulsing photons from those in the ON in 806.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A system for synchronous emission of modulated photons from two or more modulated LED lights, the system comprising:
   at least one master controller;
   a master clock within said at least one master controller, wherein said at least one master controller is capable of generating a signal transmitting the time of said master clock within said signal;
   two or more LED lights, wherein each LED light comprises:
   a controller;
   an internal clock; and
   at least one photon emitter, wherein said at least one photon emitter is capable of emission of photons;
   wherein the controller is in communication with the internal clock and the at least one photon emitter and wherein the time of the internal clock synchronizes the timing of the emission of photons from said at least one photon emitter;
   wherein each LED light is capable of receiving said signal from the master controller and wherein the controller of each LED light is capable of analyzing the time of said master clock of said signal from said master controller and comparing the time of the master clock with the time of the internal clock of the LED light.

2. The system of claim 1, wherein the time of the internal clock of each LED light of said two or more LED lights is synchronized with the master clock of at least one master controller.

3. The system of claim 1, wherein each of said two or more LED lights further comprises a temperature sensor, wherein the temperature sensor is in communication with said controller.

4. The system of claim 1, wherein each of said two or more LED lights further comprises a barometer, wherein the barometer is in communication with said controller.

5. The system of claim 1, wherein each LED light of said two or more LED lights further comprises:
   at least one antenna;
   a signal receiver, wherein said signal receiver is operably coupled to said antenna and wherein said signal receiver is in communication with said controller;
   a signal transmitter, wherein said signal transmitter is capable of emitting a signal from each of said two or more LED lights and wherein said signal transmitter is in communication with said controller.

6. The system of claim 1, wherein each master of said at least one master controller further comprises:
   at least one antenna;
   a signal receiver, wherein said signal receiver is operably coupled to said antenna and wherein said signal receiver is in communication with said controller;
   a signal transmitter, wherein said signal transmitter is capable of emitting a signal from said master and wherein said signal transmitter is in communication with said controller.

7. The system of claim 1, wherein each LED light of said two or more LED lights further comprises a power supply, wherein said power supply is operably coupled to the controller.

8. The system of claim 7, wherein said power supply is chosen from DC, AC and battery.

9. The system of claim 1, wherein the internal clock of each LED light of said two or more LED lights is capable of synchronization between 10.0 ns and 1000 ms of master clock of said at least one master controller.

10. The system of claim 1, wherein each LED light of said two or more LED lights are commissioned and paired with a master of said at least one master controller.

11. The system of claim 10, wherein said master is capable of emitting a signal to said LED light and wherein said LED light is capable of analyzing said signal from said at least one master controller and is capable of requesting said master pair with said LED light.

12. The system of claim 11, wherein said analysis by said LED light is based on the strength of the signal from said at least one master controller.

13. The system of claim 1, wherein said LED light is capable of analyzing the strength of the signal from said at least one master controller.

14. The system of claim 13, wherein said LED light emits an indicator indicating the strength of the signal from said at least one master controller.

15. The system of claim 1, wherein said signal from said master is capable of containing multiple components.

16. The system of claim 1, wherein said LED light is chosen from light emitting diodes, and incandescent lights with a mechanical modulator, fluorescent lights with a mechanical modulator, high intensity discharge lights with a mechanical modulator, High-Pressure Sodium with a mechanical modulator, Low-Pressure Sodium with a mechanical modulator, and Mercury Vapor with a mechanical modulator.

17. The system of claim 1, wherein said LED light is capable of producing a wavelength spectrum ranging from 1.0 to 1600 nm.

18. The system of claim 1, further comprising a gateway, wherein said gateway is operably linked to said at least one master controller.

19. The system of claim 18, wherein said gateway is hardwired to said at least one master controller.

20. The system of claim 1, wherein said system comprises a gateway, wherein said gateway is capable of direct communication with said two or more LED lights.

21. The system of claim 1, wherein said signal from said at least one master is communicated to each LED light of said two or more LED lights by hardwire.

22. The system of claim 21, wherein said hardwire is chosen from ethernet, waveguide, AC electrical wires, DC electrical wire and fiber-optic that supports bidirectional and unidirectional communication.

23. The system of claim 1, wherein said signal from said at least one master controller is communicated to each LED of said two or more LED lights wirelessly.

24. The system of claim 23, wherein said wireless communication is chosen from ultra-wide band, broadband, pulse radio frequency (RF), passive, Zigbee, wireless ad hoc network, mesh, and RFID.

25. The system of claim 10, wherein said LED light is capable of emitting a signal to said paired master of said at least one master controller and wherein said paired master is capable of analyzing said signal from said LED light and is capable of requesting said LED light pair with said master.

26. The system of claim 1, further comprising at least one sensor, wherein said sensor is capable of receiving said signals from said at least one master controller and wherein said sensor is capable if emitting a signal to said at least one master controller.

27. The system of claim 26, wherein said signal from said sensor is capable of containing data.

28. The system of claim 26, wherein said sensor is chosen from a smoke, heat, fire, moisture, stem diameter, GPS, feeders, waterers, weight sensors, strain gauges, Pressure transducers, accelerometers, vibration, sound and vocalization to list of measurements, vibration, sound and vocalization to list of measurements, heart rate, blood pressure, ovulation, hormone tracking, such as pheromones, estrogen, testosterone and cortisol.

29. A method of synchronizing the photon emission from two or more LED lights within an LED light array, the method comprising:
providing at least one master controller;
providing a master clock within said at least one master controller, wherein said at least one master controller is capable of generating a signal transmitting the time of said master clock within said signal;
providing two or more LED lights, wherein each LED light comprises:
a controller;
an internal clock; and
at least one photon emitter, wherein said at least one photon emitter is capable of emission of pulsed or modulated photons;
wherein the controller is in communication with the internal clock and the at least one photon emitter and wherein the time of the internal clock synchronizes the timing of the emission of photons from said at least one photon emitter;
generating a signal from said at least one master controller, wherein said signal contains the time of said master clock within said signal and the time the signal is sent;
receiving said signal within each LED light;
analyzing within the controller of said LED light the time of said master clock and the time the signal was sent from said at least one master controller; and
comparing the time of said master and the time the signal was sent from said at least one master controller with the time of the internal clock of the LED light;
and synchronizing the internal clock of the LED light with the master clock of said at least one master controller.

30. The method of claim 29, further comprising synchronizing the time of the internal clock of each LED light of said two or more LED lights with the master clock of said at least one master controller.

31. The method of claim 29, wherein each of said two or more LED lights further comprises a temperature sensor, wherein the temperature sensor is in communication with said controller.

32. The method of claim 29, wherein the internal clock of each LED light of said two or more LED lights are recalibrated by the controller based on a change in temperature from the temperature sensor.

33. The method of claim 29, wherein each of said two or more LED lights further comprises a barometric pressure sensor, wherein the barometric pressure sensor is in communication with said controller.

34. The method of claim 33, wherein the internal clock of each LED light of said two or more LED lights are recalibrated by the controller based on a change in barometric pressure from the barometric pressure sensor.

35. The method of claim 29, wherein each LED light of said two or more LED lights further comprises:
- at least one antenna;
- a signal receiver, wherein said signal receiver is operably coupled to said antenna and wherein said signal receiver is in communication with said controller; and
- a signal transmitter, wherein said signal transmitter is capable of emitting a signal from each of said two or more LED lights and wherein said signal transmitter is in communication with said controller.

36. The method of claim 29, wherein each LED light of said two or more LED lights further comprises a power supply, wherein said power supply is operably coupled to the controller.

37. The method of claim 36, wherein said power supply is chosen from DC, AC and battery.

38. The method of claim 29, further comprising synchronizing the internal clock of each LED light of said two or more LED lights within 10.0 ns to 1000 ms of the master clock of said one or more master controllers.

39. The method of claim 29, further comprising synchronizing the internal clock of each LED light of said two or more LED lights within two nanoseconds of master clock of said at least one master controller.

40. The method of claim 29, further comprising pairing each LED light of said two or more LED lights with a master of said at least one master controller.

41. The method of claim 40, emitting a signal from said master to said LED light; analyzing said signal from said master within said LED light; and requesting said master pair with said LED light.

42. The method of claim 40, emitting a signal from said master of said at least one master controller to said LED light; analyzing said signal from said master within said LED light; and requesting said LED light pair with said master of said at least one master controller.

43. The method of claim 42, wherein said analysis by said LED light is based on the strength of the signal from said master of said at least one master controller.

44. The method of claim 43, wherein said analysis by said master is based on the strength of the signal from said LED light.

45. The method of claim 29, further comprising analyzing the strength of the signal received by said LED light from said at least one master controller.

46. The method of claim 45, further comprising emitting an indicator from said LED light indicating the strength of the signal from said at least one master controller.

47. The method of claim 29, wherein said signal from said at least one master controller is capable of containing multiple data components.

48. The method of claim 47, wherein said data is chosen from unique ID, preamble, timing, recipe step, recipe, temperature, firmware, status, postamble, echoes, wrong channels, and partial messaging.

49. The method of claim 29, wherein said LED light is chosen from light emitting diodes, and incandescent lights with a mechanical modulator, fluorescent lights with a mechanical modulator, high intensity discharge lights with a mechanical modulator, High-Pressure Sodium with a mechanical modulator, Low-Pressure Sodium with a mechanical modulator, and Mercury Vapor with a mechanical modulator.

50. The method of claim 29, wherein said LED light is capable of producing a wavelength spectrum ranging from 1.0 to 1600 nm.

51. The method of claim 29, further comprising a gateway, wherein said gateway is operably linked to said at least one master controller.

52. The method of claim 51, wherein said gateway is hardwired to said at least one master controller.

53. The method of claim 52, wherein said method comprises a gateway in direct communication with said two or more LED lights.

54. The method of claim 29, further comprising communicating said signal from said at least one master to each LED light of said two or more LED lights by hardwire.

55. The method of claim 54, wherein said hardwire is chosen from ethernet, waveguide, AC electrical wires, DC electrical wire and fiber-optic that supports bidirectional and unidirectional communication.

56. The method of claim 55, wherein said a repetitive signal within said hardwire is used to cadence the photon recipe within each LED light.

57. The method of claim 29, further comprising communicating said signal from said at least one master is communicated to each LED light of said two or more LED lights wirelessly.

58. The method of claim 57, wherein said wireless communication is chosen from ultra-wide band, broadband, pulse radio frequency (RF), passive, Zigbee, wireless ad hoc network, mesh, and RFID.

59. The method of claim 29, further comprising at least one sensor, wherein said sensor receives said signals from said at least one master controller and wherein said sensor is capable if emitting a signal to said at least one master controller.

60. The method of claim 59, wherein said sensor is chosen from a smoke, heat, fire, moisture, stem diameter, GPS, feeders, waterers, wight sensors, strain gauges, Pressure transducers, accelerometers, vibration, sound and vocalization to list of measurements, heart rate, blood pressure, ovulation, hormone tracking, such as pheromones, estrogen, testosterone, and cortisol.

61. The method of claim 29, further comprising recalibrating the internal clock of each LED light of said two or more LED lights at a repetitive interval.

62. The method of claim 61, wherein said repetitive interval is between 5 seconds and 1 hour.

63. The method of claim 62, wherein the internal clock is recalibrated to account for changes in temperature.

64. The method of claim 63, wherein the internal clock is recalibrated to account for changes in barometric pressure.

65. The method of claim 29, wherein the intensity of a photon emission from said LED light is adjusted to account for the placement of the LED light, wherein the adjustment is based on a change in distance to organism.

66. The method of claim 29, wherein said two or more LED lights are synchronized to reduce the amount of time each LED light of the two or more LED lights are ON.

67. The method of claim 66, wherein the total number of LED lights of said two or more LED lights that are emitting photons at any specific time is between 5% to 90% of the total number of LED lights of said two or more LED lights.

68. The method of claim 67, further comprising:
- shifting the emission of photons from LED lights in an ON cycle to an OFF cycle and at the same time shifting 10% to 80% of the emission LED lights in an OFF cycle to an ON cycle; and
- repeating said shifting of LED lights so that 10% to 80% of the LED lights are always in an ON cycles while a corresponding percentage are in an OFF cycle.

* * * * *